United States Patent
Barclay et al.

(10) Patent No.: US 6,600,060 B2
(45) Date of Patent: Jul. 29, 2003

(54) CLA-ESTERS

(75) Inventors: Scott Barclay, Bedford (GB); Krzysztof Piotr Rakowski, Wormerveer (NL); Victoria Taran, Wormerveer (NL)

(73) Assignee: Loders Croklaan BV, Wormerveer (NL)

( * ) Notice: Subject to any disclaimer, the term of this patent is extended or adjusted under 35 U.S.C. 154(b) by 0 days.

(21) Appl. No.: 09/864,881

(22) Filed: May 25, 2001

(65) Prior Publication Data
US 2002/0049346 A1 Apr. 25, 2002

(30) Foreign Application Priority Data
Jun. 19, 2000 (EP) .......................................... 00305185

(51) Int. Cl.$^7$ .............................. C12P 7/64; A23D 9/00; C07C 57/00; C07C 69/52; C07C 67/30
(52) U.S. Cl. ........................ 554/224; 426/601; 435/134; 435/135; 560/205; 560/212; 560/220
(58) Field of Search ............................... 554/224; 560/205, 560/212, 220; 435/134, 135; 426/1

(56) References Cited

FOREIGN PATENT DOCUMENTS

| EP | 1 022 306 A1 | | 7/2000 |
|---|---|---|---|
| JP | 11263750 A | * | 9/1999 |
| WO | WO 97/18320 | | 5/1997 |
| WO | WO 99/32105 | | 7/1999 |

OTHER PUBLICATIONS

Shimada et al, Enzymatic Synthesis of L–Menthyl Esters in Organic Solvent–Free System, Journal of the American Oil Chemists Society 1999, 76(10), pp. 1139–1142.*

Garcia et al, Biotechnology Letters, vol. 20, No. 4, 1998, pp. 393–395.

* cited by examiner

Primary Examiner—Johann Richier
Assistant Examiner—Paul A. Zucker
(74) Attorney, Agent, or Firm—Morgan, Lewis & Bockius LLP

(57) ABSTRACT

The invention is concerned with esters from conjugated linoleic acid and a food allowable alcohol from the group of terpene alcohols and sesquiterpene alcohols. These esters have good taste and display the health effects from the conjugated linoleic acid (CLA) part and from the food allowable alcohol part of the molecule.

19 Claims, 1 Drawing Sheet

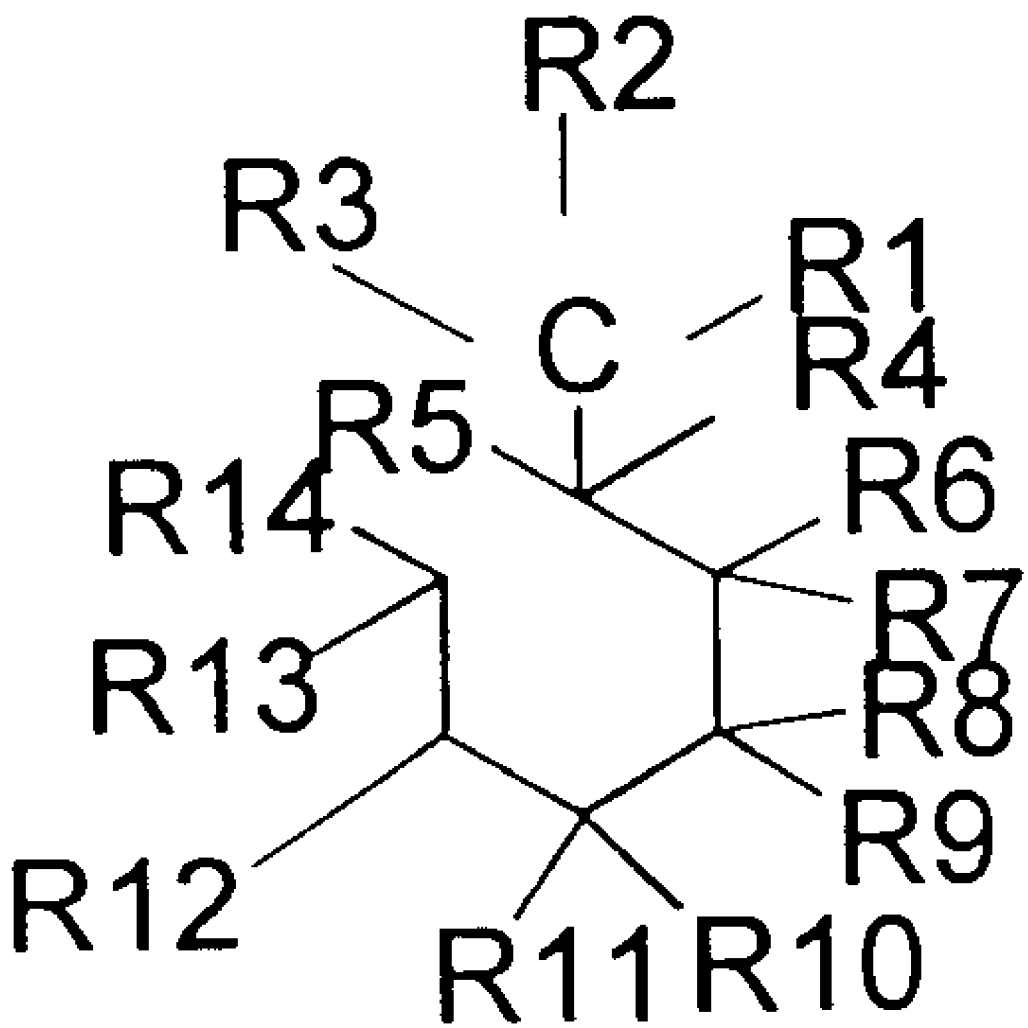
Formula 1

CLA-ESTERS

Esters from CLA (reaction product of conjugated linoleic acid and an alcohol) are known from eg WO 97/18320 or WO 99/32105. However the esters disclosed in WO 97/18320 are mainly the octylesters and these esters have the disadvantage that the alcohol residue is not food allowable and that therefore the use of these esters in foods is a problem. In this same document also glycerol esters of CLA isomers are disclosed which can be made from glycerol and free CLA by esterification. However during this esterification the enrichment in a specific CLA isomer (in general c9t11 or t10c12 CLA) is low or the reaction rate and/or yield for this conversion is very low. Moreover the products so obtained often are not very active for their desired health effect. Another problem is that the esters disclosed in WO '105 often are derived from an alcohol that, although being food allowable is not readily available or is difficult to remove from the reaction mixture (eg tocopherol alcohol or ascorbyl alcohols or retinyl alcohols).

We studied whether we could find a solution for above problems. This study resulted in the finding of new esters of CLA isomers that can be made easily in good yields in relatively short times while the products obtained often displayed high enrichment rates in specific CLA-isomers (in particular in c9t11 and/or t10c12 isomers). Moreover the alcohols used herefore are food allowable and easily available and can be separated easily from the crude reaction mix resulting from the partial conversion of the free CLA with the alcohol.

Moreover we found that these esters displayed good health properties and excellent taste properties. In particular the taste of the esters was improved compared to the taste of the free acids.

Therefore our invention concerns in the first instance with esters of conjugated linoleic acid (- CLA) and a food allowable alcohol wherein the food allowable alcohol is selected from terpene alcohols or sesquiterpene alcohols. In particular the use of the alcohols with general formula I, wherein

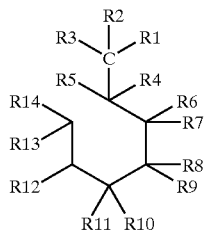

Formula 1

R1=H, or forms together with R4 a C—C bond,
R2=H or CH3
R3=H, CH3 or OH
R4=H or forms together with R1, or with R6 or with R14 a C—C bond, or forms together with R9 a —C— bridge or forms together with R9 a —C—C—C—C— residue

II (CH3)2 C—C

R5=H or forms together with R13 or with R14 a C—C bond

R6=H or forms together with R4 a C—C bond
R7=H, or OH
R8=H or OH or forms together with R10 a C—C bond
R9=H, or forms together with R4 a —C— bridge or a —C—C—C—C— residue

II (CH3)2C—C

R10=H or forms together with R8 or with R12 a C—C bond
R11=H, i-propyl, i-propenyl, CH3 or forms together with R4 a —C(CH3)2-bridge
R12=H or forms together with R10 a C—C bond
R13=H, OH, or—C(CH3)=C—C(OH)— or forms together with R5 a C—C bond
R14=H, or forms together with R4 or R5 a C—C bond lead to excellent results In particular the invention is concerned with esters derived from an alcohol selected from the group consisting of menthol, isopulegol, methenol, carveol, carvomenthenol, carvomenthol, isobornylalcohol, caryophyllenealcohol, geraniol, farnesol and citronellol. These alcohols are all food allowed, easily available and give high enrichment in specific CLA isomers when converted partially with free CLA (in particular with a 50:50 mix of c9t11 and t10c12 CLA) along an enzymic route. Moreover the esters display good activity with respect to anti inflammatory and anti diabetic or insulin resistance effects and taste far better than the free CLA where they are derived from. The esters can be obtained easily in a form wherein the esters comprise more than 80 wt %, preferably more than 90 wt % and in particular more than 95 wt % of c9t11 plus t10c12 CLA isomers. Depending on the conversion that is applied the esters can be obtained as a mix wherein the c9t11 and t10c12 CLA-isomers are present in a weight ratio of 50:50, or as a mix wherein the c9t11:t10c12 isomers are present in a weight ratio of more than 70:30, in particular more than 80:20. The esters of the enriched isomer mix have the advantage that the mix mainly will display the specific health effects from the specific isomer present in high contents while the other specific health effects of the other isomer hardly will be noticed. This enables us to dose more specifically to achieve a specific health effect, while also the dosage of the CLA compound can be less which is of particular advantage if the esters are applied as food supplement because this will limit the size of the capsules and the smaller the capsules can be, the easier they can be swallowed by the consumer.

A particular preference exists for esters of CLA and menthol wherein more than 80 wt %, preferably more than 90 wt % of the CLA residue of the esters consists of c9t11-CLA, while less than 2 wt % of the total CLA-residue consists of CLA-isomers other than c9t11 and t10c12 and the esters contain less than 5 wt % preferably less than 3 wt % of free fatty acids. Administering of these products means that potentially negative side effects of other components can be avoided.

Our invention further concerns a process for the preparation of esters of conjugated linoleic acid (CLA) and a food allowable alcohol as defined above, wherein free conjugated linoleic acid is reacted with the food allowable alcohol in the presence of less than 1.8 wt % water and a lipase. This process will result in esters that can be used in food products as both components of the products are food allowable.

In the instance that an ester is desired wherein higher contents of a specific CLA-isomer is present the above process can be adapted to a process wherein a food allowable alcohol with the formula as defined above is reacted with a mix of free CLA with about 50% of both main isomers (c9t11 and t10c12) and wherein the reaction is performed by partially converting this mixture of c9t11 and t10c12 CLA in the presence of an enzyme than can discriminate between c9t11 and t10c12-CLA isomers and which enzyme preferably is *Candida rugosa* lipase, whereupon CLA-esters are isolated enriched in c9t11 CLA-isomer and free fatty esters are isolated as unconverted reactant enriched in t10c12 CLA isomer.

Other enzymes that can be applied are lipase D; lipase QL; lipase-SL; Mucor miehei lipase, optionally on a support such as duolite; Cand antartica lipase and lipozyme.

The different products can be obtained by working up the crude reaction product as follows:

first add a diluted base to the crude reaction mixture then separate the water phase and the organic phase followed by washing of the organic phase and adjusting the pH of this phase to pH 5–7 and finally by removal of the water from this phase, preferably by distillation.

By this route esters are obtained enriched in the c9t11 CLA isomer.

To obtain a free CLA product enriched in the t10c12 isomer the procedure is as follows:

the water phase of the reaction product obtained according to above process is acidified to a pH<3.0, preferably <1.5, whereupon the mixture obtained is separated in an upper layer and a residue and the upper layer is washed with water and the water is removed therefrom.

According to another aspect of our invention our invention also concerns food products comprising a fat and a good tasting health component wherein the taste and health component is an ester according to the invention. The food products are specifically selected from the group consisting of spreads (10–90% fat contents); dressings, mayonnaise, cheese, ice cream, ice cream coatings; confectionery coatings or fillings; sauces and culinary products. These food products suitably contain 0.5 to 20 wt % of our novel CLA esters.

Our novel esters can also be used for the preparation of triglycerides containing CLA residues. Therefore an ester composition according to the invention can be converted with glycerol or with a vegetable oil in the presence of a base or an enzyme while in the instance that glycerol is converted the liberated alcohol residue from the esters of the CLA-esters is removed from the reaction mix during the conversion. This removal of liberated alcohol can be done by vacuum distillation or by molecular distillation.

According to a last embodiment our invention also concerns the use of our CLA esters as a good tasting health agent, in particular having anti-inflammatory or anti-diabetic or insulin resistant properties.

EXAMPLES

1) CLA menthol esters:

2.5 g CLA 50:50, 80% main isomers (cis9,t11, t10,c12)

0.02 g demineralized water 0.4 g menthol 0.026 g *Candida rugosa* lipase

T 38° C.

Reaction time 22 hours

Mix well 2.5 g CLA with 0.02 g water. Add 0.4 g menthol and mix very well for 30 mm in shaker at 38° C. and 200 rpm. Add this mixture to 0.026 g *Candida rugosa* lipase; mix everything very well. Put the mixture in the shaker at 38° C. and 200 rpm. After 22 hours add to the reaction mixture 30 ml isooctane/ethanol (1:1) and 33 ml 0.2 N NaOH. Mix very well. Centrifuge for 5 min at 3500 rpm. Separate the organic phase from the aqueous phase. Wash the organic phase 3×100 ml of demineralized water and evaporate the solvent.

Add aqueous phase to 50 ml $H_2SO_4$ (1:10) and 30 ml isooctane. Remove the organic phase and wash 3×100 ml of demineralized water. Evaporate the solvent. The analysis of free fatty acids (FFA) and menthol esters fractions are shown in table below:

| Fatty acid residue | Fame of CLA FFA | Fame of CLA menthol esters |
|---|---|---|
| C16:0 | 2.4 | 2.3 |
| C16:1 | 0.1 | 0.1 |
| C18:0 | 2.5 | 1.7 |
| CLA,t,t | 2.8 | 0.6 |
| CLAc9,c11 | 1.1 | 0.4 |
| CLAc10,c12 | 1.3 | 0.4 |
| CLAc11,c13 | 0.6 | 0.9 |
| C18:1,t | 1.1 | 0.0 |
| C18:1,c | 10.8 | 13.7 |
| CLA-OX | 0.0 | 0.2 |
| C18:2,t | 0.4 | 0.6 |
| C18:2c | 2.1 | 3.6 |
| C20:0 | 0.7 | 0.1 |
| C20:1 | 0.3 | 0.0 |
| C22:0 | 0.1 | 0.1 |
| CLA,c9,t11 | 28.1 | 62.1 |
| CLA,t10,c12 | 45.5 | 13.2 |
| Ratio c9,t11:t10,c12 | 38:62 | 83:17 |
| Conversion | 32% | |
| FFA, % | 99.3 | 1.85 |

2) CLA geraniol ester:

20 g CLA 50:50

3.64 g geraniol 0.24 g demineralized water 0.2 g *Candida rugosa* lipase

T 38° C.

Reaction time 1 hour

The CLA, geraniol and water were mixed in a vial and incubated in a shaking water bath at 38° C. After 30 minutes the lipase was added, mixed by shaking and the vial replaced in the water bath. After 1 hour the reaction mixture was diluted with an equal volume of cold hexane and filtered through a 0.45 μm PTFE membrane to remove the enzyme. After evaporation of the solvent 17 g of the remaining oil was dissolved in 100 ml of hexane and mixed with 100 ml of demin water in which 2.84 g of sodium hydroxide had been dissolved. After vigorous shaking, 10 ml of ethyl alcohol was added to ease the separation of the layers.

The aqueous phase was removed and added to 100 ml of a 20% hydrochloric acid solution and 100 ml of hexane and shaken vigorously. The organic layer was removed and washed with 3×100 ml of demin water, 100 ml of brine and the solvent evaporated to leave 14 g of oil comprising 85% FFA.

The organic phase was washed with 2×100 ml of hot alkaline demin water, 100 ml of demin water and 100 ml of brine. The dry organic phase was passed through a column of basic alumina to remove any traces of remaining FFA and the solvent evaporated to yield 3 g of oil.

| | ester | ffa |
|---|---|---|
| C16:0 | 4.91 | 4.33 |
| C16:1 | 0.22 | 0 |
| C18:0 | 0.69 | 1.98 |
| CLA tt | 0.82 | 4.31 |
| CLA c9,c11 | 0.39 | 1.38 |
| CLA c10,c12 | | 1.3 |
| CLA c11,c13 | 0.93 | 0.52 |
| C18:1 t | 0.12 | 0.16 |
| C18:1 c | 36.12 | 23.13 |
| CLA-ox | 0 | 0 |
| C18:2 t | 1.15 | 0.95 |
| C18:2 c | 2.64 | 1.52 |
| C20:0 | 0 | 0 |
| C20:1 | 0 | 0.2 |
| C22:0 | 0 | 0.24 |
| CLA c9,t11 | 44.7 | 20.62 |
| CLA t10,c12 | 7.31 | 39.36 |
| Conversion | 30% | |
| RATIO | 85.9 | 34.4 |

The two product fractions were examined by TLC and the respective bands for FFA and ester removed and worked up for FAME analysis. FAME analysis is a method wherein the fatty acid composition is measured by chromatography as the methyl esters of the fatty acids.

3) CLA citronellol ester:

5 g CLA 1.1 g citronellol 0.06 g demineralized water 0.1 g *Candida rugosa* lipase

T 30° C.

Reaction time 30 minutes

The CLA, citronellol and water were mixed in a vial and incubated in a shaking water bath at 30° C. After 30 minutes the lipase was added, mixed by shaking and the vial replaced in the water bath. After 30 minutes the reaction mixture was filtered through a 0.45 μm PTFE membrane to remove the enzyme. The reaction had reached 20% conversion.

The reaction mixture was analysed by TLC. The ester bands were worked up for FAME analysis.

| | |
|---|---|
| C16:0 | 2.89 |
| C16:1 | 0.21 |
| C18:0 | 0.71 |
| C18:1 | 9.98 |
| C18:2 | 1.47 |
| C20:0 | 0.47 |
| C20:1 | 0.28 |
| C22:1 | 0.41 |
| CLA c9,t11 | 39.65 |
| CLA t10,c12 | 7.65 |
| CLA c,c | 1.78 |
| CLA t,t | 6.99 |
| Conversion | 20% |
| Ratio | 84:16 |

What is claimed is:

1. An ester of conjugated linoleic acid and a food allowable alcohol, wherein the food allowable alcohol is a terpene alcohol or a sesquiterpene alcohol.

2. An ester of conjugated linoleic acid (CLA) and a food allowable alcohol according to claim 1 wherein the terpene alcohol or sesquiterpene alcohol is selected from the group consisting of alcohols of formula I

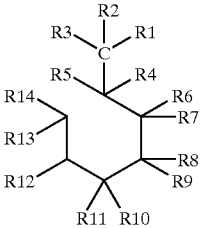

Fomula 1 wherein:

R1 is H, or forms together with R4 a C—C bond,

R2 is H or CH3

R3 is H, CH3 or OH

R4 is H or forms together with R1, or with R6 or with R14 a C—C bond, or forms together with R9 a —C— bridge or forms together with R9 a

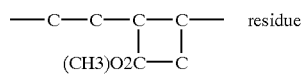 residue

R5 is H or forms together with R13 or with R14 a C—C bond

R6 is H or forms together with R4 a C—C bond

R7 is H, or OH

R8 is H or OH or forms together with R10 a C—C bond

R9 is H, or forms together with R4 a —C— bridge or a

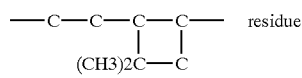 residue

R10 is H or forms together with R8 or with R12 a C—C bond

R11 is H, 1-propyl, 1-propenyl, CH3 or forms together with R4 a —C(CH3)2-bridge

R12 is H or forms together with R10 a C—C bond

R13 is H, OH, or —C(CH3)=C—C(OH)— or forms together with R5 a C—C bond

R14 is H, or forms together with R4 or R5 a C—C bond.

3. An ester according to claim 1 wherein the alcohol is selected from the group consisting of menthol, isopulegol, methenol, carveol, carvomenthenol, carvomenthol, isobornylalcohol, caryophyllenealcohol, geraniol, farnesol and citronellol.

4. An ester according to claim 2 wherein the CLA residue of the ester comprises more than 80 wt % of c9t11 plus t10c12 CLA isomers.

5. An ester according to claim 4 wherein the c9t11 and t10c12 CLA-isomers are present in a weight ratio of 50:50.

6. An ester according to claim 4 wherein the c9t11:t10c12 isomer weight ratio in the CLA-ester is more than 70:30.

7. An ester of conjugated linoleic acid (CLA) and menthol wherein more than 80 wt % of the CLA residue of the ester consists of c9t11-CLA, while less than 2 wt % of the total CLA-residue consists of CLA-isomers other than c9t11 and t10c12 and the ester contains less than 5 wt % of free fatty acids.

8. A process for the preparation of an ester of conjugated linoleic acid (CLA) and a food allowable alcohol as defined in claim 1, wherein free conjugated linoleic acid is reacted with a food allowable alcohol in the presence of less than 1.8 wt % water and a lipase.

9. A process for the preparation of esters of CLA and a food allowable alcohol with the formula as defined in claim 2 wherein the esters obtained are enriched in c9t11 and t10c12 CLA in a weight ratio of about 50:50 and the food allowable alcohol in the presence of an enzyme that can discriminate between c9t11 and t10c12-CLA isomers, whereupon CLA-esters are isolated as unconverted reactant enriched in t10c12 CLA isomer.

10. The process according to claim 9 wherein the crude reaction mixture obtained is worked up by:

first adding a diluted base to the crude reaction mixture separating the water phase and the organic phase washing of the organic phase and adjusting the pH of this phase to pH 5-07 removal of the water from this phase.

11. The process for the preparation of a free conjugated linoleic acid (CLA) mixture enriched in t10c12-CLA wherein:

the water phase of the reaction product obtained according to the process of claim acidified to a pH<3.0;

the mixture obtained is separated in an upper layer and a residue and the upper layer is washed with water and the water is removed therefrom.

12. A food product comprising a fat and a health component wherein the health component is at least one ester according to claim 1.

13. A food product according to claim 12 wherein the food product is selected from the group consisting of spreads, dressings, mayonnaise, cheese, ice cream, ice cream coatings; confectionery coatings or fillings; sauces and culinary products.

14. A food product according to claim 12 wherein the food product contains, based on total product weight, 0.5 to 20 wt % of the ester.

15. A process for the preparation of triglycerides wherein at least one of the fatty acid residues is a conjugated linoleic acid residue wherein an ester according to claim 1 is converted with glycerol or with a vegetable oil in the presence of a base or an enzyme while in the instance that glycerol is converted, the liberated alcohol residue from the esters of the CLA-esters is removed from the reaction mix during the conversion.

16. An ester according to claim 4 containing 95 wt % of c9t11 plus t10c12 CLA isomers.

17. An ester according to claim 7 containing less than 3 wt % of free fatty acids.

18. The process of claim 9 wherein the enzyme is *Candida rugosa* lipase.

19. The process of claim 11 wherein the water phase is acidified at a pH of<1.5.

* * * * *